US011712214B2

(12) United States Patent
Castillo et al.

(10) Patent No.: US 11,712,214 B2
(45) Date of Patent: *Aug. 1, 2023

(54) SYSTEM AND METHOD FOR DETERMINING RESPIRATORY INDUCED BLOOD MASS CHANGE FROM A 4D COMPUTED TOMOGRAPHY

(71) Applicant: William Beaumont Hospital, Royal Oak, MI (US)

(72) Inventors: Edward Castillo, Houston, TX (US); Thomas Guerrero, Rochester Hills, MI (US)

(73) Assignee: William Beaumont Hospital, Royal Oak, MI (US)

( * ) Notice: Subject to any disclaimer, the term of this patent is extended or adjusted under 35 U.S.C. 154(b) by 98 days.

This patent is subject to a terminal disclaimer.

(21) Appl. No.: 17/188,174

(22) Filed: Mar. 1, 2021

(65) Prior Publication Data

US 2021/0393230 A1    Dec. 23, 2021

Related U.S. Application Data

(63) Continuation of application No. 16/325,902, filed as application No. PCT/US2017/047623 on Aug. 18, 2017, now Pat. No. 10,932,744.

(Continued)

(51) Int. Cl.
*G06T 11/00* (2006.01)
*A61B 6/00* (2006.01)
(Continued)

(52) U.S. Cl.
CPC .............. *A61B 6/5217* (2013.01); *A61B 5/02* (2013.01); *A61B 5/7253* (2013.01); *A61B 6/032* (2013.01);
(Continued)

(58) Field of Classification Search
CPC .. A01K 27/009; A01K 5/0275; A01K 29/005; A01K 11/006; G06Q 10/0635;
(Continued)

(56) References Cited

U.S. PATENT DOCUMENTS

2007/0032732 A1    2/2007  Shelley et al.
2013/0303899 A1*  11/2013  Mistry .................. A61B 6/486
                                                                600/425

(Continued)

FOREIGN PATENT DOCUMENTS

JP    2005-28121 A     2/2005
JP    2006-526460 A   11/2006
(Continued)

OTHER PUBLICATIONS

International Search Report and Written Opinion for PCT/US2017/047623 dated Aug. 18, 2017.

(Continued)

*Primary Examiner* — Phuoc H Doan
(74) *Attorney, Agent, or Firm* — Honigman LLP; Thomas Appledorn; Jonathan P. O'Brien

(57)    ABSTRACT

A method for determining respiratory induced blood mass change from a four-dimensional computed tomography (4D CT) includes receiving a 4D CT image set which contains a first three-dimensional computed tomographic image (3D CT) and a second 3D CT image. The method includes executing a deformable image registration (DIR) function on the received 4D CT image set, and determining a displacement vector field indicative of the lung motion induced by patient respiration. The method further includes segmenting the received 3D CT images into a first segmented image and a second segmented. The method includes determining the change in blood mass between the first 3D CT image and the (Continued)

second 3D CT image from the DIR solution, the segmented images, and measured CT densities.

16 Claims, 7 Drawing Sheets

Related U.S. Application Data

(60) Provisional application No. 62/376,511, filed on Aug. 18, 2016.

(51) Int. Cl.

| | | |
|---|---|---|
| *G06T 7/37* | (2017.01) | |
| *G06T 7/11* | (2017.01) | |
| *A61B 6/03* | (2006.01) | |
| *A61B 5/02* | (2006.01) | |
| *G06T 7/00* | (2017.01) | |
| *G06T 3/00* | (2006.01) | |
| *G06T 7/262* | (2017.01) | |
| *A61B 5/00* | (2006.01) | |

(52) U.S. Cl.
CPC ............ *A61B 6/466* (2013.01); *A61B 6/5235* (2013.01); *A61B 6/5288* (2013.01); *A61B 6/541* (2013.01); *G06T 3/0068* (2013.01); *G06T 3/0081* (2013.01); *G06T 3/0093* (2013.01); *G06T 7/00* (2013.01); *G06T 7/0016* (2013.01); *G06T 7/11* (2017.01); *G06T 7/262* (2017.01); *G06T 7/37* (2017.01); *G06T 2207/10076* (2013.01); *G06T 2207/20048* (2013.01); *G06T 2207/20116* (2013.01); *G06T 2207/20221* (2013.01); *G06T 2207/30061* (2013.01); *G06T 2207/30104* (2013.01)

(58) Field of Classification Search
CPC ......... G06T 7/0014; G06T 7/11; G06T 7/187; G06T 3/40; G06T 7/70; A61B 5/1118; G06N 5/046; G06F 15/18; A01J 5/007
See application file for complete search history.

(56) References Cited

U.S. PATENT DOCUMENTS

| | | | |
|---|---|---|---|
| 2015/0379706 A1 | 12/2015 | Leonhardt et al. | |
| 2016/0113614 A1* | 4/2016 | Cetingul ............ | A61B 6/5205 382/131 |

FOREIGN PATENT DOCUMENTS

| | | |
|---|---|---|
| JP | 2010-057795 A1 | 3/2010 |
| JP | 2011-212313 A | 10/2011 |
| JP | 2013-39427 A | 2/2013 |
| JP | 2013-192912 A | 9/2013 |
| JP | 2014-193409 A | 10/2014 |
| JP | 2014-210171 A | 11/2014 |
| JP | 2016-047294 A | 4/2016 |
| WO | WO2011/092982 A1 | 8/2011 |

OTHER PUBLICATIONS

Castillo, Richard, et al. "Spacial correspondence of 4D CT ventilation and SPECT pulmonary perfusion defects in pateitns with malignant airway stenosis" Phys. Med. Biol. 57 (2012) 1855-1871.
Extended Search Report for EP17842218.4 dated Feb. 7, 2020.
Mistry, N., et al. "Pulmonary Ventilation and Perfusion Imaging Using 4DCT" Medical Physics, vol. 38, No. 6, Jun. 2011 WE-G-214-06.
Yamamoto, Tokihiro, et al. "Four-dimensional computed tomography pulmonary ventilation images vary with deformable image registration algorithms and metrics" Med. Phys. 38(3), Mar. 2011 p. 1348-1358.
Extended Search Report for EP21216104 dated May 4, 2022.
Japanese Patent Office, Office Action for Application 2021-177490 dated Oct. 26, 2022.

* cited by examiner

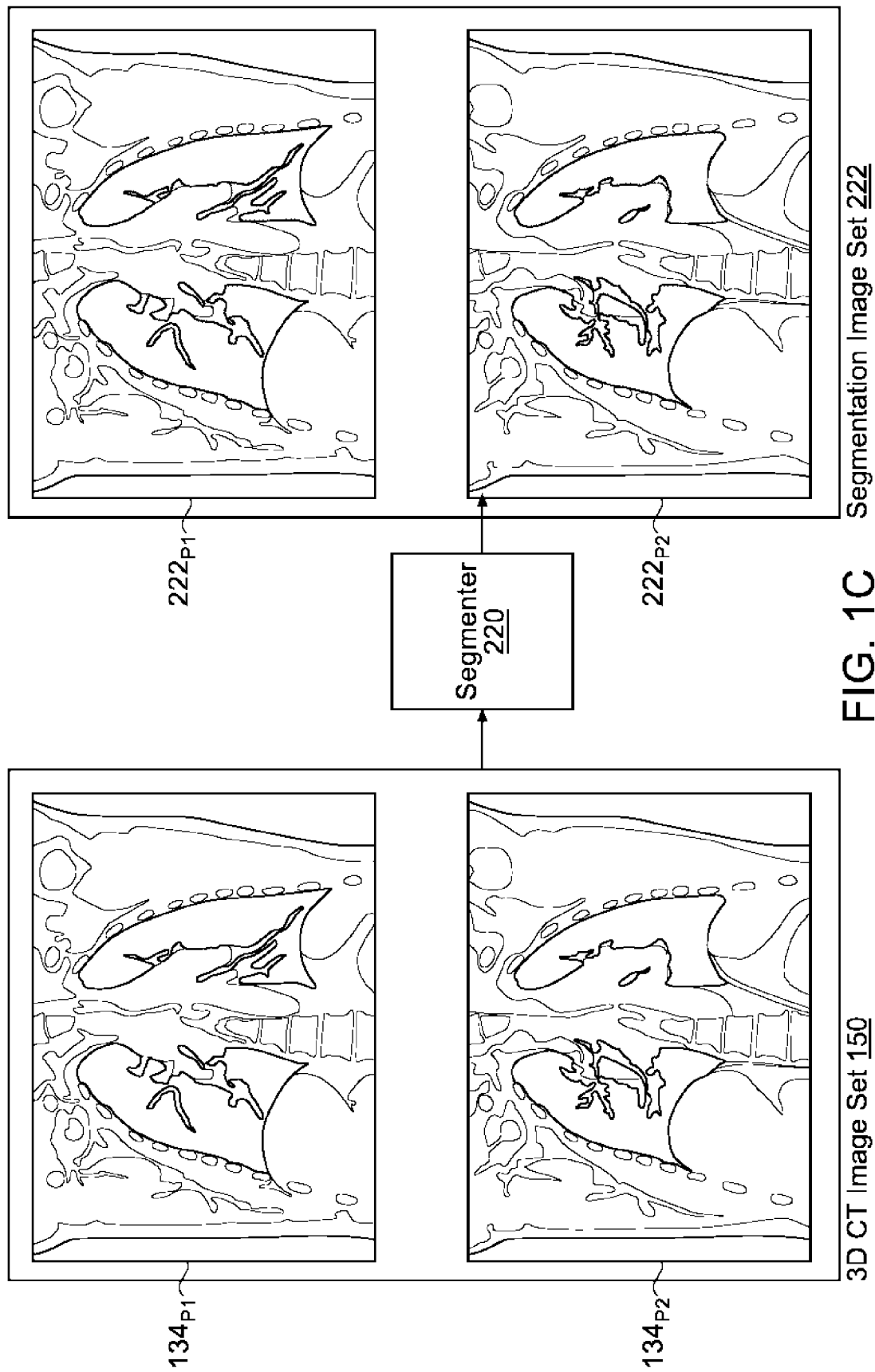

SYSTEM AND METHOD FOR DETERMINING RESPIRATORY INDUCED BLOOD MASS CHANGE FROM A 4D COMPUTED TOMOGRAPHY

CROSS REFERENCE TO RELATED APPLICATIONS

This patent application is a continuation of U.S. application Ser. No. 16/325,902 filed Feb. 15, 2019, which claims the benefit of PCT International Application No. PCT/US2017/047623 filed Aug. 18, 2017, which claims the benefit under 35 U.S.C. § 119(e) to U.S. Provisional Application 62/376,511, filed on Aug. 18, 2016. The disclosures of the prior applications are considered part of the disclosures of these applications and are hereby incorporated by reference in their entireties.

TECHNICAL FIELD

This disclosure relates to a system and method for determining respiratory induced blood mass changes from a four-dimensional computed tomography.

SUMMARY

One aspect of the disclosure provides a method. The method may include receiving, at a data processing hardware, a four-dimensional computed tomography (4DCT) image set comprised of a series of three-dimensional computed tomography images (referred to as phases) which depict respiratory motion within the thoracic region. The data processing hardware may determine a spatial transformation(s) between different phases of the 4DCT. The data processing hardware determines a blood mass change (for each voxel location) within the thoracic region based on the spatial transformation(s) and the 4DCT image values. The data processing hardware outputs respiratory-induced blood mass change image(s) that describes the blood mass differences between different 4DCT phases.

Implementations of the disclosure may include one or more of the following optional features. For example, the data processing hardware may execute a deformable image registration (DIR) function on the 4DCT phases. Further, the data processing hardware may segment the individual 4DCT phases.

In some implementations, the data processing hardware may compute a deformable image registration that maps spatially corresponding voxel locations across the 4DCT phases. The deformable image registrations may be in the form of displacement vector fields, the displacement vector fields indicative of lung motion induced by breathing of a patient. A displacement vector field may include a plurality of vectors, each of the vectors indicative of spatially corresponding points within a pair of three-dimensional computed tomography image phases.

In some examples, the method further comprises delineating, by the data processing hardware, a first plurality of subvolumes within a reference three-dimensional computed tomography image phase included in the 4DCT. The data processing hardware may warp each of first plurality of the subvolumes onto a second target three-dimensional computed tomography image phase included in the 4DCT. Warping each of the first plurality of subvolumes includes estimating a mass change for each of the subvolumes.

In some implementations, the reference three-dimensional computed tomography image is taken as a first phase of the respiratory cycle and the second target three-dimensional computed tomography image is taken as a second phase of the respiratory cycle. The first phase may be a full inhale phase and the second phase may be a full exhale phase.

In further examples, determining the blood mass change includes determining, by the data processing hardware, a sum of a blood mass change for a plurality of subvolumes.

Another aspect of the disclosure provides a system comprising data processing hardware and memory hardware. The memory hardware in communication with the data processing hardware, the memory hardware storing instructions that when executed on the data processing hardware cause the data processing hardware to perform operations comprising. One of the operations may include receiving four-dimensional computed tomography image set, which includes a first three-dimensional computed tomography image of a volume and a second three-dimensional computed tomography image of the volume. Another operation includes determining a spatial transformation from the first three-dimensional computed tomography image to the second three-dimensional computed tomography image. Further operations include determining a blood mass change within the lung region based on the spatial transformation and CT values, and outputting a respiratory-induced blood mass change image based on the determined blood mass change.

The details of one or more implementations of the disclosure are set forth in the accompanying drawings and the description below. Other aspects, features, and advantages will be apparent from the description and drawings, and from the claims.

BACKGROUND

Pulmonary embolism (PE) refers to a blockage of an artery in the lung. Often, PE is the result of a blood clot (thrombus) from within the deep veins of the legs breaking off and flowing towards the lungs. PE can be fatal within the first hour of symptoms. Accordingly, accurate detection and treatment of PE is highly time sensitive.

Pulmonary computed tomography angiography (CTA) is one method used to detect PE. CTA is a computed tomography technique used to visualize arterial and venous vessels throughout the body, which include arteries serving the brain, lungs, kidneys, arms, and legs. Although highly accurate, CTA may be harmful to a patient when overused, as it includes radiation exposure and the possibility of identifying clinically insignificant PE that may not require treatment treated. Furthermore, CTA requires the administration of a radiographic dye (e.g., iodinated contrast) to enhance the visibility of vascular structures within the body. This iodinated contrast may cause renal insufficiency (i.e., kidney failure) or an allergic reaction in some patients. Thus, although CTA is highly accurate, some patients may be ineligible for the procedure.

As an alternative, a single photon emission computed tomography (SPECT) perfusion scan may be acquired. SPECT perfusion is a nuclear medicine imaging modality based on the $^{99m}$Tc-labeled macro-aggregates of albumin ($^{99m}$Tc-MAA) tracer. Because this is a highly-specialized procedure, SPECT image acquisition often requires transporting the patient to a remote nuclear medicine clinic, many of which only operate during normal business hours. Consequently, emergency room patients may not have immediate access to SPECT. Furthermore, SPECT perfusion requires a prolonged image acquisition time (20-30) minutes, and may undesirably delay diagnosis of a highly time-sensitive PE.

Therefore, it is desirable to have an imaging system that overcomes the aforementioned deficiencies of the CTA and SPECT modalities.

DESCRIPTION OF DRAWINGS

FIG. 1C is a schematic view of a segmenter of the imaging system of FIG. 1A.

Like reference symbols in the various drawings indicate like elements.

DETAILED DESCRIPTION

Figure 1A:
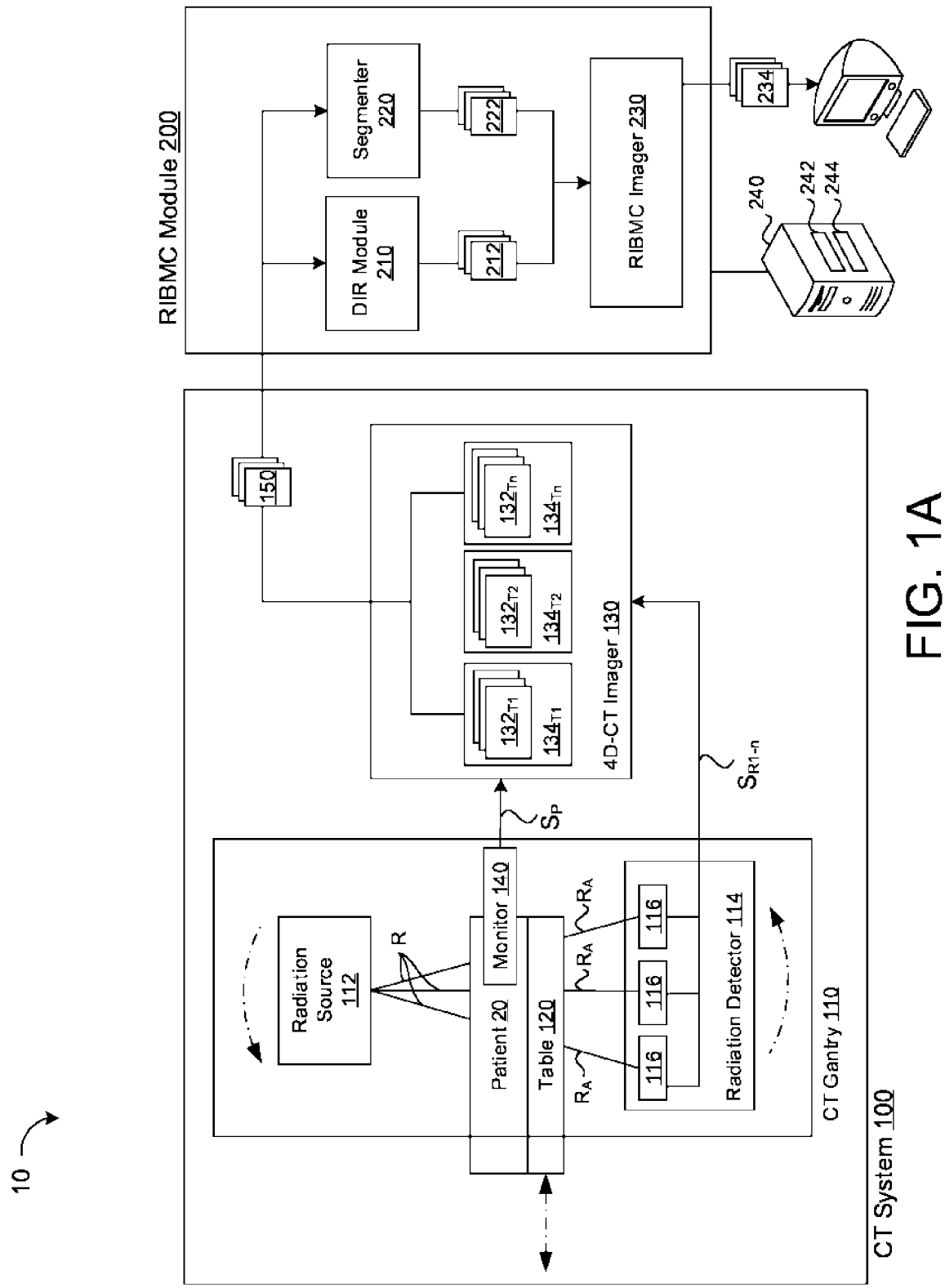
FIG. 1A is a schematic view of an imaging system that generates respiratory induced blood mass change images.

This disclosure provides an imaging system and method for detecting perfusion defects using a 4D CT imaging system, which is readily available in many emergency centers. The disclosure describes the imaging system and method as applied to the lungs of a patient. However, the system and method may be applied to other organs as well.

Perfusion is the process of a body delivering blood to a capillary bed in its biological tissue. During normal breathing blood mass within the lugs is known to fluctuate as a result of a variable return of blood to the heart during a respiratory cycle. The disclosed imaging system and method extracts blood flow information related to the change of the blood mass within the lungs throughout the respiratory cycle. The blood flow information is then used to identify areas of the lungs corresponding to perfusion defects, such as regions of hypo-perfusion induced by pulmonary emboli or obstructions.

Referring to FIG. 1, an example of an imaging system 10 according to one implementation of the disclosure is provided. In some examples, the imaging system 10 includes a four-dimensional computer tomography (4D-CT) imaging system 100, as is known in the art, and a respiratory-induced blood mass change (RIBMC) module.

The 4D-CT imaging system 100 includes a gantry 110, a table 120, and a 4D-CT imager 130. As shown, the table 120 may be operable to move between a first position, where a patient 20 is disposed within the gantry 110, and a second position, where the patient 20 is removed from the gantry 110. Alternatively, the gantry 110 may move with respect to the table 120.

The gantry 110 includes a radiation source 112 and a radiation detector 114 placed on diametrically opposite sides of a horizontal rotational axis of the gantry 110. The radiation source 112 and the radiation detector 114 are configured to rotate in unison about a horizontal axis of the gantry 110 during a scan. A position of the table 120 may be adjusted so that a longitudinal axis of the patient 20 is substantially aligned with the rotational axis of the gantry 110. Accordingly, the radiation source 112 and the radiation detector 114 will rotate about the longitudinal axis of the patient 20 during the scan.

Generally, the radiation source 112 emits a radiation beam R (e.g., x-rays), which passes through the patient 20, and is received by the radiation detector 114. In some examples, the radiation detector 114 may include an array of detector elements 116 which are configured to receive a fan-like radiation beam R from the radiation source 112. In other examples, the radiation detector 114 may be a multi-slice radiation detector 114 that includes a plurality of detector rows (not shown) each including an array of the radiation detector elements 116. The multi-slice radiation detector 114 is configured to receive a cone-like radiation beam R from the radiation source 112.

As the radiation beam R passes through the patient 20, different tissues of the body absorb the radiation beam R at different rates, and the radiation beam R becomes an attenuated radiation beam $R_A$. Portions of the attenuated radiation beam $R_A$ are received by the detector elements 116, whereby each of the portions of the attenuated radiation beam $R_A$ may have a different intensity, depending on the amount of the radiation beam R absorbed by the patient 20 in the respective portion. The detector elements 116 each emit a radiation signal SR corresponding to the respective intensity of the portion of the attenuated radiation beam $R_A$.

The radiation signals $S_{R1-n}$ are communicated from each of the detector elements 116 to the imager 130, which translates the radiation signals $S_{R1-n}$ into two-dimensional (2D) CT images 132, or slices, corresponding to the scanned areas of the patient 20. The imager 130 is further configured to compile and arrange the 2D CT images 132 to construct a plurality of three-dimensional (3D) CT images 134 representing the scanned region of the patient 20. The 3D CT images 134 are, in turn, sequentially arranged to form four-dimensional (4D) CT image sets representing a period of the respiratory cycle, as discussed further, below.

The CT system 100 may include a respiratory monitor 140 configured to track the respiratory cycle of the patient 20. In some examples, the respiratory monitor 140 may physically measure the patient 20 to determine a phase $P_1$-$P_n$ of the respiratory cycle. For example, an abdominal belt or vision system may track measurements of the thorax corresponding to inhalation and exhalation. Alternatively, the respiratory monitor 140 may be integrated in the imager 130, whereby the 2D CT images 132 or 3D CT images 134 are evaluated by the imager 130 to determine the breathing cycle phase. For example, variation in a diaphragm or an anterior surface of the patient 20 in the 2D CT images 132 and/or the 3D CT images 134 may be referenced by the imager 130 to identify the phase $P_1$-$P_n$ of the respiratory cycle.

The respiratory monitor 140 may provide a signal $S_P$ representing the phase $P_1$-$P_n$ of the respiratory cycle to the imager 130. The imager 130 may then use the signal $S_P$ to sort the 2D CT images 132 into bins, which correspond to a respective phase of the respiratory cycle. Each phase $P_1$-$P_n$ represents a percentage of a period of a repeating respiratory cycle. In some implementations, each phase $P_1$-$P_n$ may correspond to a time period (t). For example, each respiratory cycle may be divided into several time periods $t_1$-$t_n$ of equal duration. Additionally or alternatively, the phases $P_1$-$P_n$ may correspond to a position within the respiratory cycle. For example, the phases $P_1$-$P_n$ may correspond to a full inspiration position, a full expiration position, and/or an intermediate position, as determined by the monitor 140.

Once the 2D CT images 132 are binned according to phase $P_1$-$P_n$, the imager 130 may construct respective three-dimensional (3D) CT images $134_{P1}$-$134_{Pn}$, each corresponding to one of the phases $P_1$-$P_n$ of the respiratory cycle. The 3D CT images 134 are then sequentially arranged according to phase $P_1$-$P_n$. and a 4D CT image set 150 is constructed, representing a desired portion of the respiratory cycle or several respiratory cycles.

The RIBMC module 200 is configured to receive the 4D CT image set 150, and to output a RIBMC image 234 based on a series of inferences and calculations, as discussed in detail, below.

With continued reference to FIG. 1A, the RIBMC module 200 includes a deformable image registration (DIR) module 210, a segmenter 220, and a RIBMC imager 230, which are described in greater detail, below. The RIBMC module 200 may be configured to operate on a server 240 having data processing hardware 242 and memory hardware 244. Alternatively, the RIBMC module 200 may be an internal device to the CT system 100 (e.g., hardware or software of the CT system 100). In some implementations, the RIBMC module 200, may be configured to interpret the 4D CT images 150 or to interact with the 4D CT imager 130.

With reference to FIGS. 1B-1E, the RIBMC module 200 is configured to receive and evaluate the 4D CT image sets 150 to provide RIBMC images 234 based on a CT measured density. Generally, CT measured density, denoted as p, is defined in terms of Hounsfield Units (HU):

$$\rho_{voxel} = \frac{mass_{voxel}}{volume_{voxel}} = 1 + \frac{HU_{voxel}}{1000}. \quad (1)$$

Mathematically, the phases $P_1$-$P_n$ of the 4D CT image set 150 represent snapshots of an HU defined density function $\rho(x, t)$. The RIBMC module 200 computes the RIBMC image 234 by using a pair (or sequence) of phases from the 4D CT images 150:

$$P(x)=\rho(x,t_1) \quad (2A)$$

and $$Q(x)=\rho(x,t_2) \quad (2B)$$

where the time points $t_1$, $t_2$ correspond to a first respiratory cycle phase $P_1$ and a second respiratory cycle phase $P_2$ (such as full inhale and full exhale), respectively. In other words, the RIBMC imager 200 computes the mass change between spatially corresponding locations at $t_1$ and $t_2$.

Figure 1B:
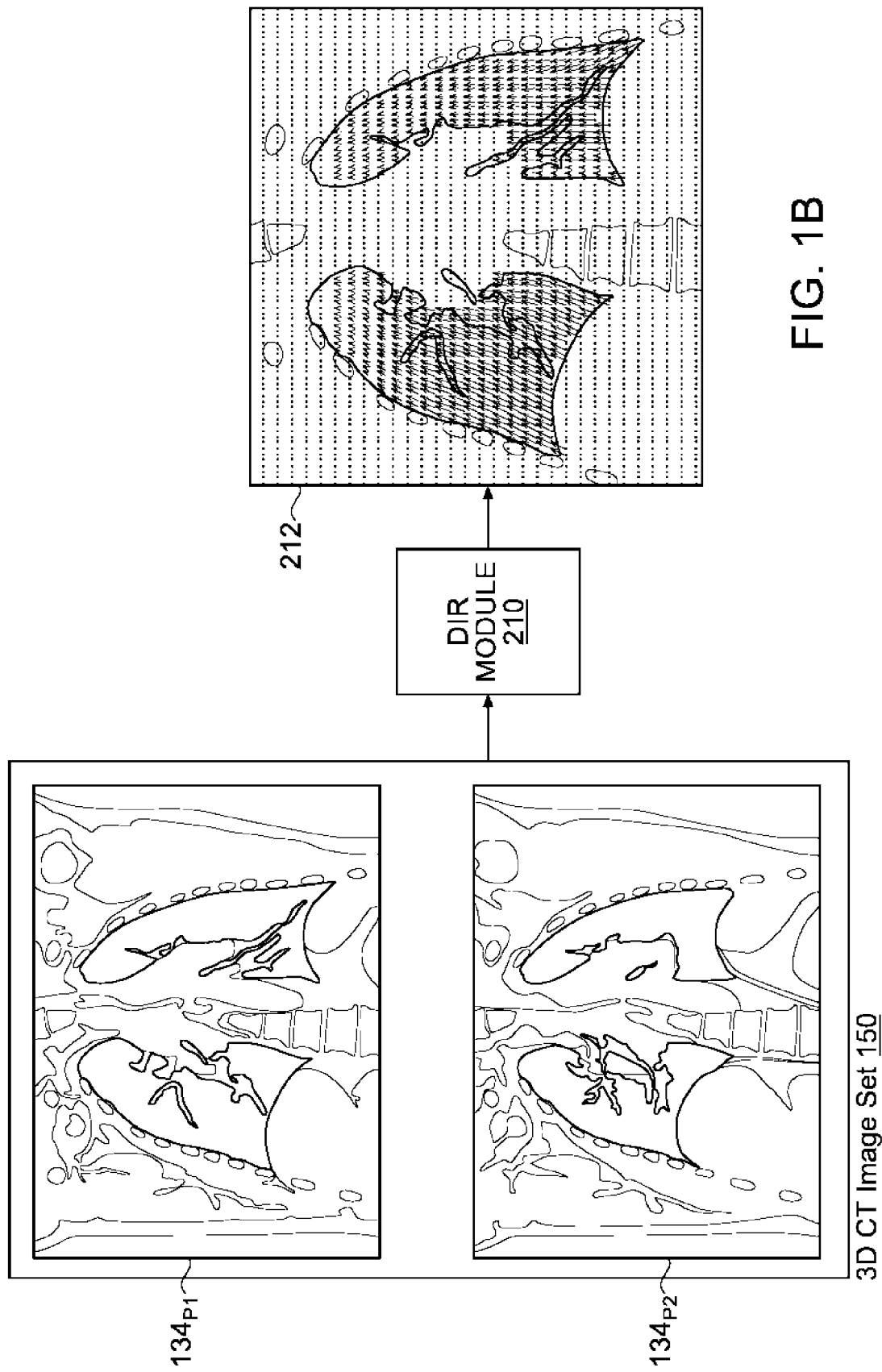
FIG. 1B is a schematic view of a deformable image registration (DIR) module of the imaging system of FIG. 1A.

In one implementation of the disclosure, the DIR module 210 of the RIBMC module 200 is configured to receive the 4D CT image set 150 and execute a DIR function on the 4D CT image set 150 to generate a spatial transformation. With reference to FIG. 1B, the 4D CT image set 150 includes a first 3D CT image $134_{P1}$ corresponding to the first time $t_1$ and a second 3D CT image $134_{P2}$ corresponding to the second time point $t_2$. In the illustrated example, the first respiratory cycle phase $P_1$ corresponds to full inhale and the second respiratory cycle phase $P_2$ corresponds to full exhale. However, intermediate time points $t_n$ may be incorporated into the DIR function and RIBMC computation.

Generally, the spatial transformation defines a geometric relationship between each voxel in the first 3D CT image $134_{P1}$ and a corresponding voxel in a second 3D CT image $134_{P2}$ of the image set 150. The first 3D CT image $134_{P1}$ includes reference points whose coordinate values are known precisely at the time point $t_1$. The second image $134_{P2}$ includes reference voxels whose coordinate values are known at the second phase $t_2$. As such, the spatial transformation provides the relationship between the position of lung tissue during, for example, full inhale and the position of the same lung tissue during full exhale.

The DIR module is configured to generate a spatial transformation, $\phi(x)$: $\mathbb{R}^3 \to \mathbb{R}^3$, that maps voxel locations in P (being the first image at a first phase $t_1$) onto their corresponding positions in Q (being a second image at a second phase $t_2$). A position of a voxel is inferred based upon its position relative to other voxels, i.e., its position in the data structure that makes up a single volumetric image. Therefore, the transformation $\phi(x)$ is often defined in terms of a displacement field d(x), (see 212 in FIG. 1B):

$$\phi(x)=x+d(x) \quad (3)$$

where x is an initial position of the voxel. The transformation $\phi(x)$ represents the respiratory induced motion of the lungs, and enables direct comparison between the density values P, Q, and consequently, the total mass of a lung region at the two phases $t_1$, $t_2$.

With continued reference to FIG. 1B, the DIR module provides a DIR registration solution 212 with respect to the first 3D CT image $134_{P1}$ and the second 3D CT image $134_{P2}$. The DIR displacement field d(x) is superimposed on the first 3D CT image $134_{P1}$ (full inhale). The base of each vector denotes a first position of a voxel at the first time point $t_1$ (full inhale) while the tip of the vector provides a corresponding second position of the voxel at the second time point $t_2$ (full exhale).

With reference to FIG. 1C, the segmenter 220 is configured to evaluate the 3D CT images $134_{P1}$, $134_{P2}$ to delineate lung parenchyma (i.e., alveoli, alveolar ducts, and respiratory bronchioles) from other structure, including vasculature and possible tumors, so that a desired RIBMC signal may be isolated. More specifically, segmenter 220 executes a segmentation algorithm based on, for example, fitting a bimodal-Gaussian mixture distribution to CT values contained in an initial lung volume mask or region of interest (ROI). Radiation intensities with a higher probability of belonging to the smaller mean are taken to be the lung parenchyma segmentation, considering that vasculature is typically denser and has a higher CT value. Additionally, or alternatively, the segmenter 220 may execute other segmentation algorithms, such as those based on machine learning. As shown in FIG. 1C, the segmenter 220 evaluates the 4D CT image set 150, including the first 3D CT image $134_{P1}$ and the second 3D CT image $134_{P2}$, and provides a region of interest (ROI) image set 222, including a first segmented image $224_{P1}$ and a second segmented image $224_{P2}$. As shown, in the segmented images $222_{P1}$, $222_{P2}$ blood veins and any other organs except the lung parenchyma are segmented out.

In some examples, if a tumor exists on the lung tissue, since the blood mass calculation is only applied to the lung tissue, the RIBMC calculation does not consider the tumor. For example, if a patient 20 has a tumor in or around his or her lungs, the RIBMC computation does not perform its calculations on the tumor. Therefore, any later calculations are also not performed on the tumor.

In some examples, the RIBMC image is computed with respect to the full lung region of interest, as shown in FIG. 1C without isolating the parenchyma. In these cases, all tissue, including blood vessels and possible tumors, are incorporated into the RIBMC calculation.

The RIBMC imager 230 is configured to compute the RIBMC image 234 from the 4D CT image set 150 based on the DIR image 212 and the ROI image set 222.

Initially, the RIBMC imager 230 calculates a mass within a reference volume $\Omega$ (i.e., the lung volume) at the time point $t_1$ and the time point $t_2$, and then determines a difference ($\Delta$Mass) between the respective masses. The mass of the lung parenchyma in the first phase may be expressed mathematically as the integral of a density function $\rho(x, t)$ over a volume $\Omega$:

$$\text{Mass}(\Omega, t_1) = \int_\Omega \rho(x, t_1) dx. \quad (4)$$

At the time point $t_2$ the reference volume $\Omega$ is displaced and deformed due to respiratory lung motion (i.e., exhalation and inhalation). The DIR transformation $\phi$ in EQ. 3 defines the deformed volume as $\hat{\Omega} = \phi(\Omega)$ so that the mass contained in the warped reference volume may be expressed as:

$$\text{Mass}(\hat{\Omega}, t_2) = \int_{\phi(\Omega)} \rho(x, t_2) dx. \quad (5)$$

Thus, the mass change $\Delta$Mass ($\Omega$, $t_1$, $t_2$) with respect to the reference volume $\Omega$ and the time points $t_1$, $t_2$ may be determined by the RIBMC imager 230 by executing the function:

$$\Delta\text{Mass}(\Omega, t_1, t_2) = \int_\Omega \rho(x, t_1) dx - \int_{\phi(\Omega)} \rho(x, t_2) dx. \quad (6)$$

Though conceptually straightforward, RIBMC is numerically challenging to compute due to practical inconsistencies. For example, resolution of the computation is limited to a resolution of the images 212, 222. Due to a contractive nature of exhalation lung motion, it is likely that an inhale-to-exhale DIR transformation $\phi$ will result in multiple first time point $t_1$ voxels being mapped into a single second time point $t_2$ voxels. Accordingly, a one-to-one relationship may not exist between voxels at the first time point $t_1$ and the second time point $t_2$. Likewise, the fixed resolution of the images 212, 222 may prevent a single second time point voxel from being mapped to multiple first time point voxels when executing the DIR transformation $\phi$ from exhale-to-inhale.

Because of the uncertainty of the DIR transformation $\phi$, in some examples, the RIBMC imager 230 determines the RIBMC image 234 by performing calculations based on numerically approximating the integrals of EQ. 6 for a series of different reference subvolumes $\Omega_k$, k=1, 2, . . . n. Thus, the density integrals must be numerically approximated from the DIR images 212 and the ROI image set 222 provided by the DIR module 210 and the segmenter 220, respectively. Given that the image grid includes rectangular voxels, the RIBMC imager 230 approximates the density integrals Mass($\Omega$, $t_1$) by summing the density values $P(x_i)$ of all the voxels contained within the subvolume $\Omega_{k1\text{-}kn}$ of interest, i.e., $x_i \in \Omega$:

$$\text{Mass}(\Omega, t_1) \approx \Sigma_{x_i \in \Omega} P(x_i). \quad (7)$$

The quadrature method used in EQ. 7 is known as a lattice rule. The error E in these types of approximations depends on a resolution of the discretization:

$$\epsilon(N) = O(N^{-r/3}), \quad (8)$$

for functions with bounded derivative up to order r. EQ. 8 indicates that the accuracy of the quadrature approximation increases as the resolution of the discretization increases. For the approximation defined by EQ. 7, N=|$\Omega$|, i.e., N is equal to the number of voxels within each subvolume $\Omega_k$, k=1, 2, . . . n. Since the resolution of the image grid is fixed and cannot be refined, the approximation accuracy of the RIBMC integrals defined by EQ. 6 depends on the number N of voxels contained in the subvolumes $\Omega_k$, k=1, 2, . . . , n, and $\phi(\Omega_k)$ (i.e., the warped subvolumes $\Omega_k$). Consequently, a strategy of taking each voxel to be its own subvolume may result in an error polluted RIBMC image 234.

Employing larger subvolumes (subvolumes) in EQ. 6 improves the accuracy of the quadrature estimate for the mass of the region, but convolves the mass change contributions of individual voxels. As such, the RIBMC imager 230 may first estimate the blood mass change over n reference subvolumes $\Omega_k$, k=1, 2, . . . n, of the lungs defined on the first 3D CT image $134_{P1}$ and the second 3D CT image $134_{P2}$. The blood mass changes for individual voxels are then inferred from the regional observations using an optimization-based image processing approach similar to those used in image deblurring.

Figure 1D:
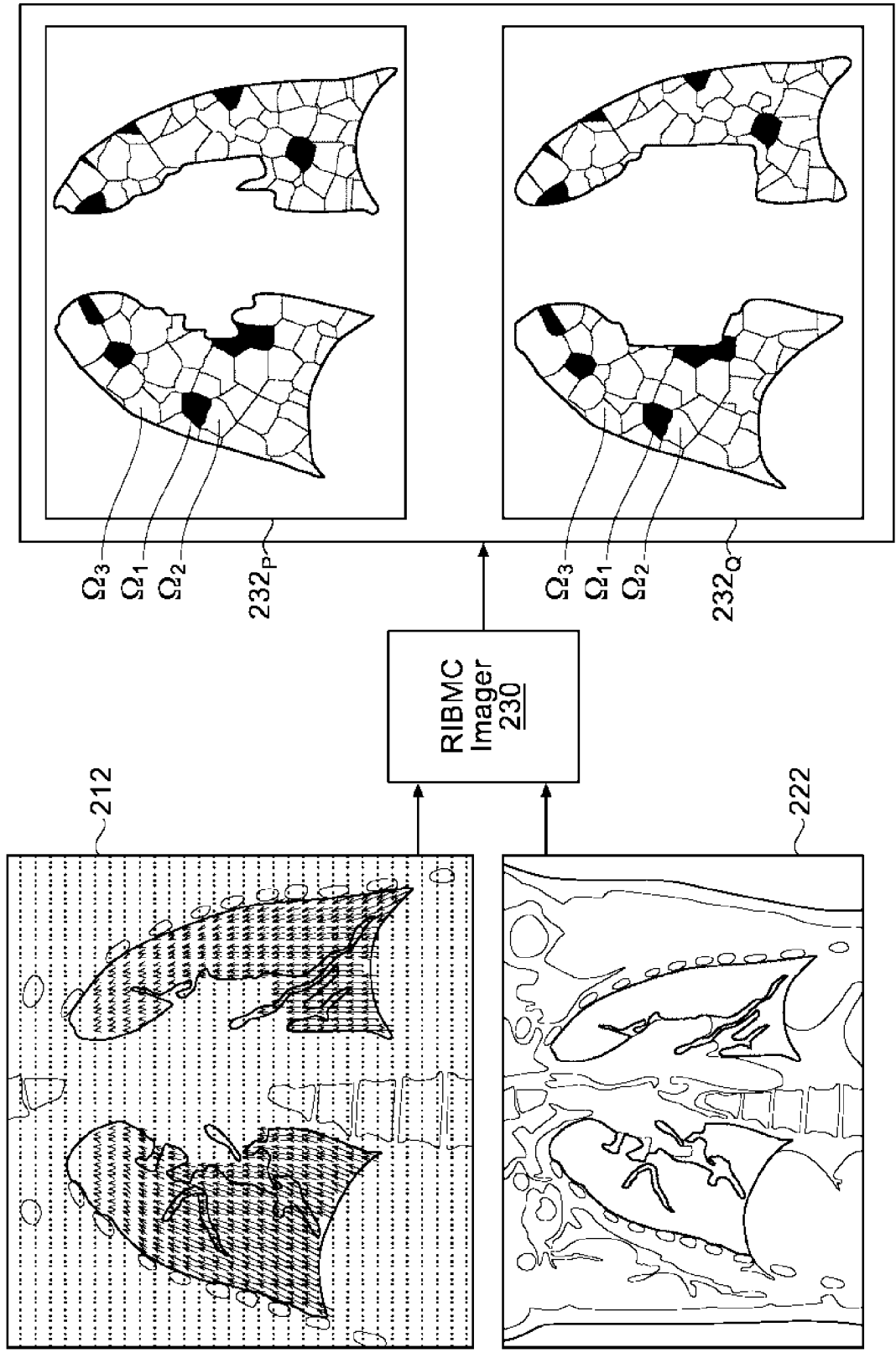
FIG. 1D is a schematic view of mapping and warping subvolumes based on the DIR across two 4DCT phases, as computed within the respiratory induced blood mass change (RIBMC) imager of the imaging system of FIG. 1A.

The RIBMC imager 230 may generate subvolumes, $\Omega_k$, k=1, 2, . . . n by applying the k-means clustering algorithm to the full lung volume ROI defined on P (see FIG. 1D). The RIBMC imager 200 may use other method to generate the n sub-regions $\Omega_k$, k=1, 2, . . . n. As shown in FIG. 1D, the lung volume subdivision image $232_P$ is defined with a plurality of the subvolumes $\Omega_k$, k=1, 2, . . . n. The subvolumes $\Omega_k$, k=1, 2, . . . n, are relatively large for the sake of clarity and illustration. However, it will be appreciated that any number n of subvolumes $\Omega_k$, k=1, 2, . . . n, may be selected, and that the sizes of the subvolumes $\Omega_k$ are independent of the number of subvolumes selected, and that the subvolumes may or may not overlap with one another.

The RIBMC imager 230 may also generate a subvolume for each individual voxel in the lung region of interest. In such cases, the number of subvolumes, n, is equal to the total number of voxels in the lung segmentation.

With the subvolumes $\Omega_k$, k=1, 2, . . . n, defined, the RIBMC imager evaluates and maps, according to the deformable image registration transformation, the subvolumes $\Omega_k$, k=1, 2, . . . n, in the first image $232_P$ onto their corresponding spatial positions in a second image $232_Q$, corresponding to the second time point $t_2$. The mapped subvolumes are defined mathematically as $\hat{\Omega}_k = \phi(\Omega_k)$. Thus, the estimated mass change $\Delta$Mass($\Omega_k$, $t_1$, $t_2$) for each subvolume $\Omega_k$ is approximated as:

$$\Delta\text{Mass}(\Omega_k, t_1, t_2) \approx \Sigma_{x_i \in \Omega_k} \hat{P}(x_i) - \Sigma_{x_j \in \hat{\Omega}_k} \hat{Q}(x_j), \quad (9)$$

where the adjusted images $\hat{P}$, $\hat{Q}$, respect the binary lung segmentation masks. For example, $$\hat{P}(x_i) = \begin{cases} P(x_i) & \text{if } B_P(x_i) = 1 \\ 0 & \text{if } B_P(x_i) = 0 \end{cases}, \quad (10)$$

where $B_p$ is a binary ROI image 222 (shown in FIG. 1D when a parenchyma segmentation is utilized and in FIG. 1C when the full long volume is utilized).

A mathematical representation of the RIBMC image 234, denoted U(x), provides the measured mass change that occurs between the first time point $t_1$ and the second time point $t_2$ of the 4D CT image set 150 for each of the voxels contained in the ROI image set 222. The regional mass change estimates provided by EQ. 9 are related to the individual voxel mass changes through a consistency constraint. Specifically, the sum of the voxel mass changes contained in the subvolumes $\Omega_k$, k=1, 2, . . . n, should equal the total regional mass change:

$$\Sigma_{x_i \in \Omega_k} U(x_i) = \Delta\text{Mass}(\Omega_k, t_1, t_2), k=1, 2, \ldots n \quad (11)$$

Taken together, the n constraints may be represented as a linear system of equations:

$$Cu = b$$

$$C \in \mathbb{R}^{n \times N}, b \in \mathbb{R}^{n \times 1}, u \in \mathbb{R}^{N \times 1}, \quad (12)$$

where $\mathbb{R}^{\{k \times 1\}}$ denotes a k-dimensional vector of real numbers, $u_i = U(x_i)$, and $b_i = \Delta Mass(\Omega_i, t_1, t_2)$, and $$C_{ij} = \begin{cases} 1 & \text{if } x_j \in \Omega_i \\ 0 & \text{otherwise} \end{cases}. \quad (13)$$

Factors such as image noise and segmentation errors suggest that EQ. 12 should not be incorporated as a hard constraint. Moreover, EQ. 12 is not guaranteed to provide enough information to uniquely determine u. Consequently, an additional assumption on the behavior of u is needed to regularize the problem of inferring u from EQ. 12.

Considering that blood mass change deficits with sharp boundaries are possible in unhealthy lungs, the RIBMC imager 200 employs a total variation (TV) model. A TV regularizer assumes that the unknown image U varies smoothly between sharp edges or discontinuities. Mathematically, this is modeled by minimizing the norm of the image gradient. The RIBMC imager 230 employs a penalty function formulation defined by EQ. 12 and the TV regularizer, the minimizer of which is the RIBMC image U*:

$$\min_u \frac{\alpha}{2} \|Cu - b\|^2 + \sum_{x_i} \|\nabla U(x_i)\|. \quad (14)$$

Figure 1E:
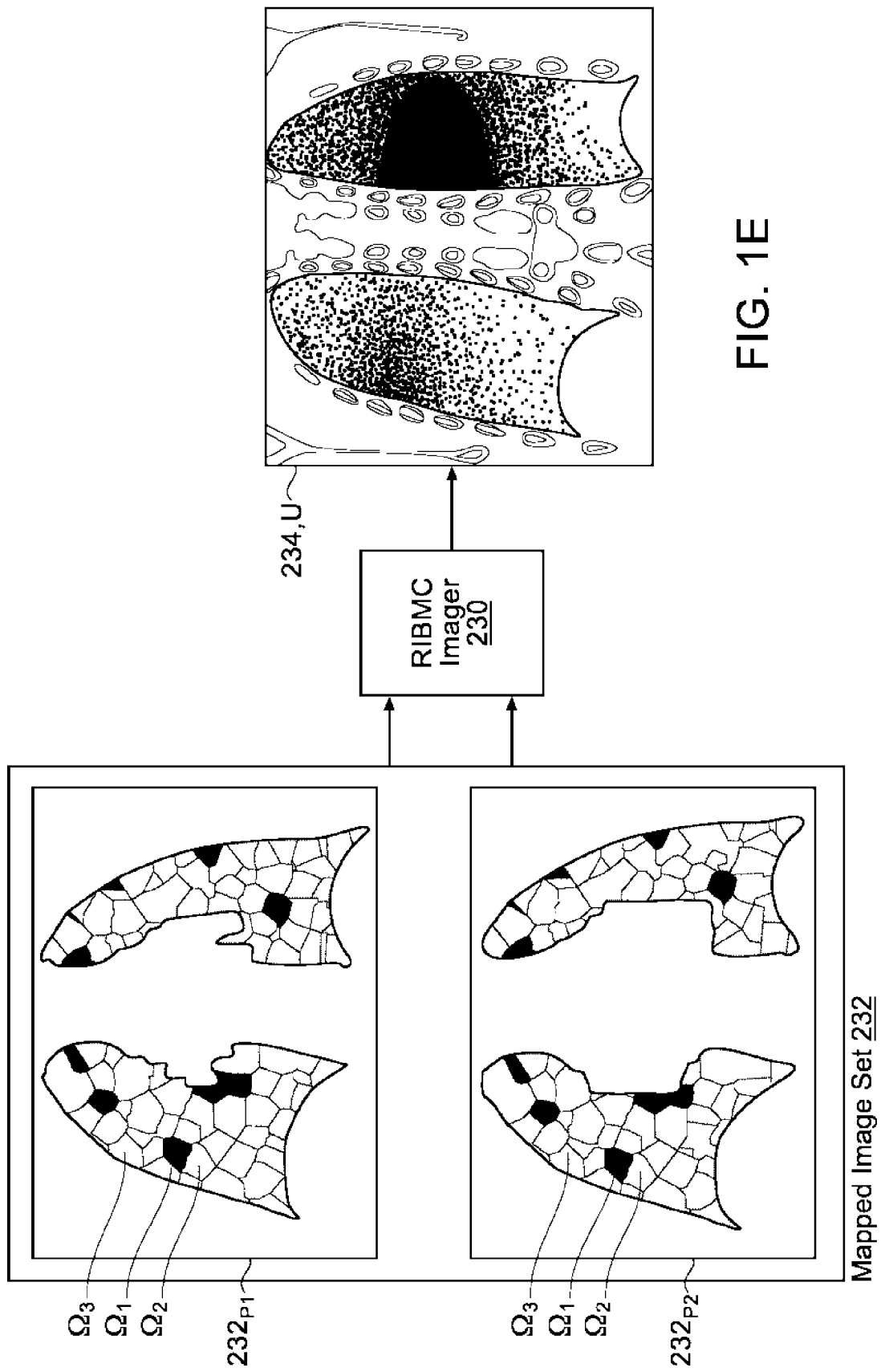
FIG. 1E is a schematic view of the RIBMC imager of the imaging system of FIG. 1A, where the RIBMC imager is generating a RIBMC image.

The penalty parameter α dictates the degree to which the solution respects both aspects of the model. Intuitively, a larger value of α may respect the mass estimates at the expense of smoothness (image regularity), whereas smaller α may generate smoother RIBMC images 234, as shown in FIG. 1E. Therefore, the RIBMC imager 230 uses the ROI image set 222 shown in FIG. 1C to determine the RIBMC image 234, U*, which is a visualization of the quantified blood mass change. The RIBMC image 234, U*, as described, is determined by executing Eq. 14. However, other methods for determining the RIBMC image 234, U* may also be used.

Referring again to FIG. 1E, brighter regions of the RIBMC image 234 indicate a relatively large amount of blood mass change (with respect to the 4D CT time points $t_1$, $t_2$), while the darker colors indicate very little or no blood mass change. The colors include a spectrum of colors with the darkest color indicative of the least blood mass change and the lightest is indicative of the most blood mass change. For example, a black spot may indicate a perfusion cold spot therein, which may correspond to the presence of a tumor or a vasculature blockage (such as a pulmonary embolism).

The RIBMC module 200 include a graphic processing unit (GPU) for calculating the DIR images 212, the ROI images 222, the mapped images 232, and or the RIBMC images 234. The GPU is a specialized electronic circuit designed to rapidly manipulate and alter memory to accelerate the creation of images in a frame buffer intended for output to a display. However, a non-display GPU card for scientific computing may also be used.

As described, the imaging system 100 may advantageously be used to produce RIBMC images 232 of the lungs of a patient 20 without the use of a contrast, as the lung tissue and the blood have a natural contrast between them. Other organs of a patient's body that create a natural contrast with blood may also be imaged using the imaging system 100.

Figure 2:
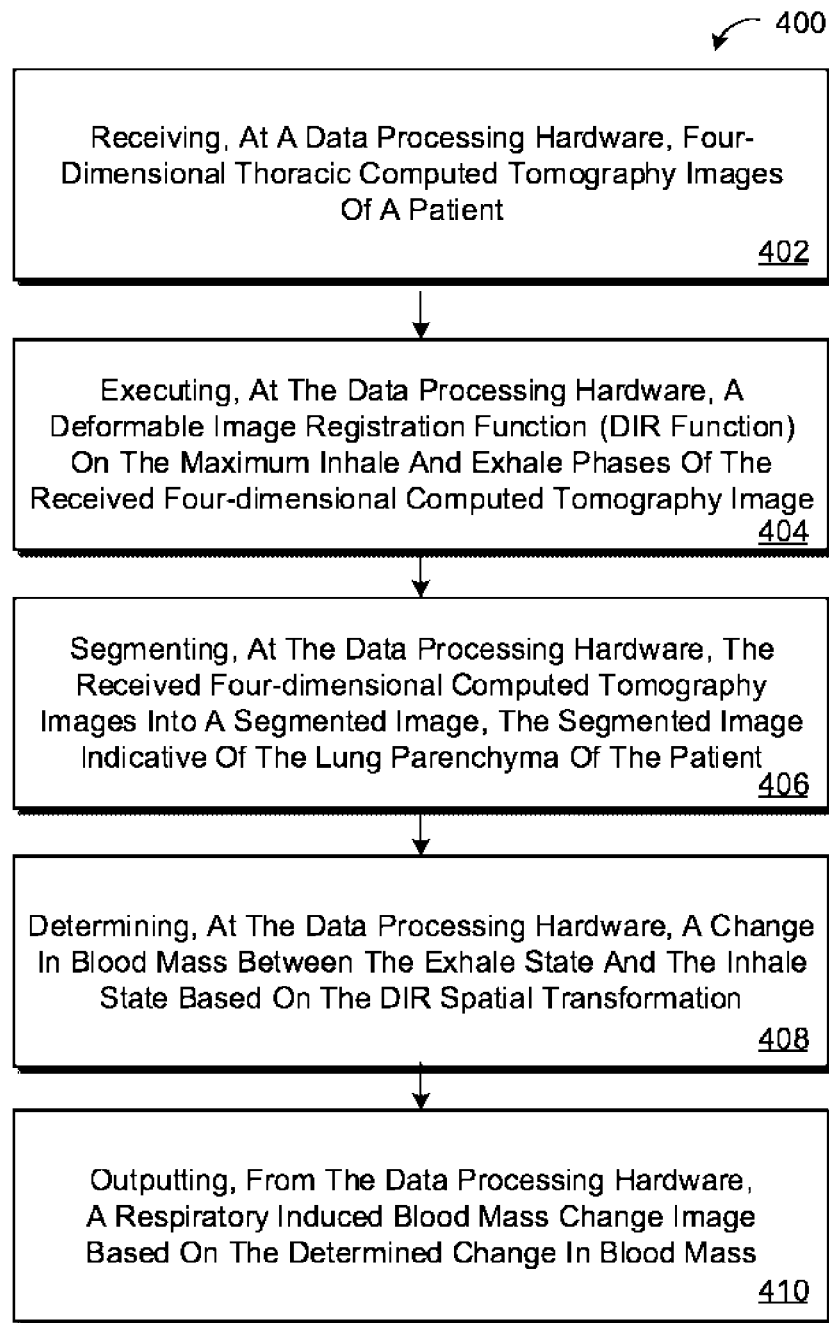
FIG. 2 is a schematic view of an exemplary arrangement of operations for outputting an RIBMC image.

FIG. 2 illustrates an exemplary arrangement of operations for a method 400 of determining and outputting a RIBMC image 234. At block 402, the method 400 includes receiving, at a RIBMC imager 230 including data processing hardware, 4D CT image set 150 of a thoracic region of a patient 20. Each 4D CT image set 150 contains a maximum inhale and maximum exhale phase (RIBMC may be computed for any pair of phases). At block 404, the method 400 includes executing, at the RIBMC imager 230, a deformable image registration function (DIR function) on the maximum inhale and exhale phases of the received 4D CT image set 150. At block 406, the method 400 includes segmenting, at the RIBMC imager 230, the received 4D CT images 150 into a segmented image 222, the segmented image 222 indicative of the lung volume and/or the lung parenchyma of the patient 20. At block 408, the method 400 includes determining, at the RIBMC imager 230, a change in blood mass between the exhale state and the inhale state based on a DIR spatial transformation and the CT values. At block 410, the method 400 includes outputting, from the RIBMC imager 230, a respiratory induced blood mass change image 234 based on the determined spatial distribution of changes in blood mass.

Figure 3:
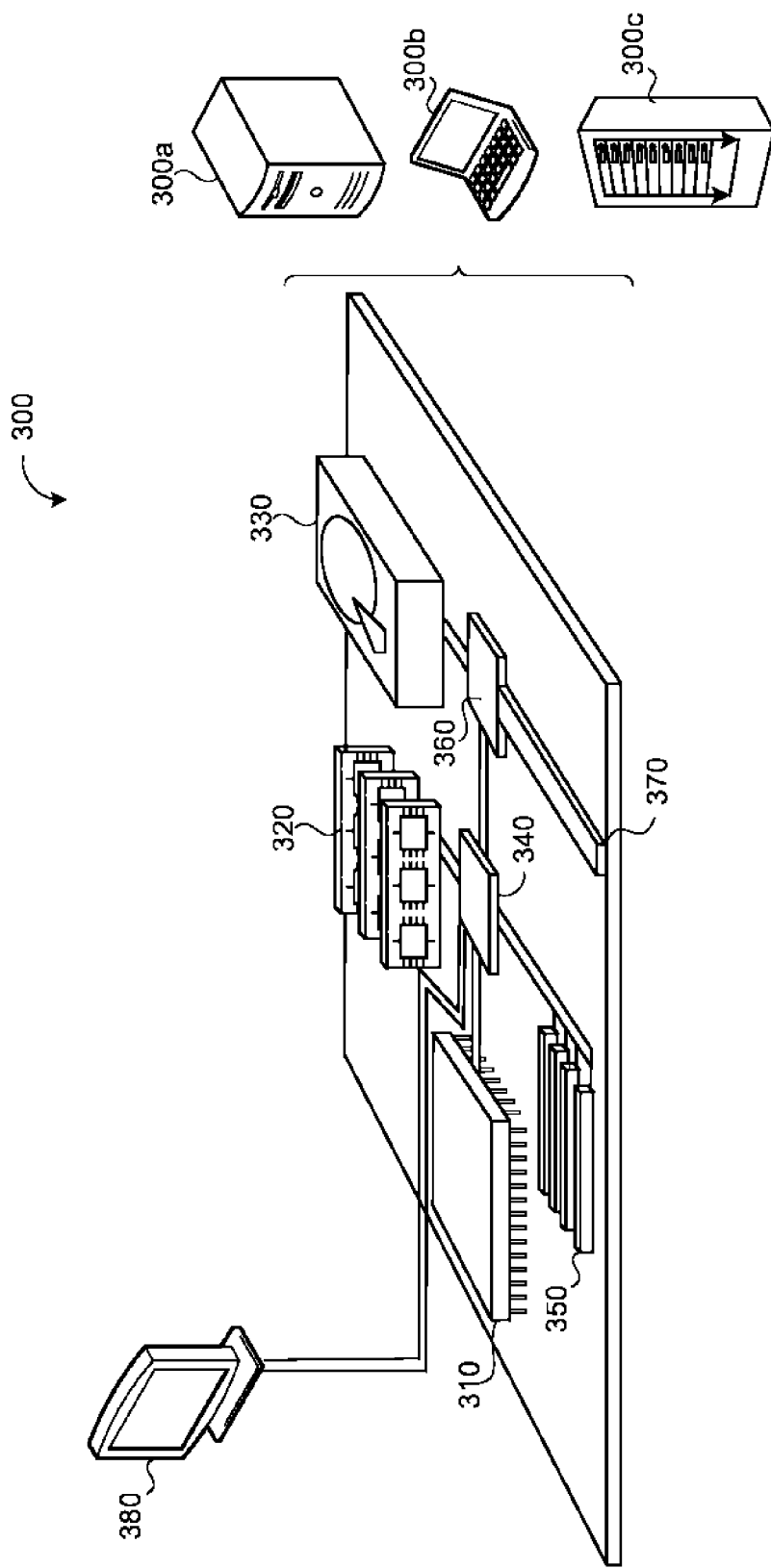
FIG. 3 is a schematic view of an example computing device executing any systems or methods described herein.

FIG. 3 is a schematic view of an example computing device 300 that may be used to implement the systems and methods described in this document. The computing device 300 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 300 includes a processor 310, memory 320, a storage device 330, a high-speed interface/controller 340 connecting to the memory 320 and high-speed expansion ports 350, and a low speed interface/controller 360 connecting to low speed bus 370 and storage device 330. Each of the components 310, 320, 330, 340, 350, and 360, are interconnected using various busses, and may be mounted on a common motherboard or in other manners as appropriate. The processor 310 can process instructions for execution within the computing device 300, including instructions stored in the memory 320 or on the storage device 330 to display graphical information for a graphical user interface (GUI) on an external input/output device, such as display 380 coupled to high speed interface 340. In other implementations, multiple processors and/or multiple buses may be used, as appropriate, along with multiple memories and types of memory. In addition, multiple computing devices 300 may be connected, with each device providing portions of the necessary operations (e.g., as a server bank, a group of blade servers, or a multi-processor system).

The memory 320 stores information non-transitorily within the computing device 300. The memory 320 may be a computer-readable medium, a volatile memory unit(s), or non-volatile memory unit(s). The non-transitory memory 320 may be physical devices used to store programs (e.g., sequences of instructions) or data (e.g., program state information) on a temporary or permanent basis for use by the computing device 300. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 330 is capable of providing mass storage for the computing device 300. In some implementations, the storage device 330 is a computer-readable medium. In various different implementations, the storage device 330 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 320, the storage device 330, or memory on processor 310.

The high speed controller 340 manages bandwidth-intensive operations for the computing device 300, while the low speed controller 360 manages lower bandwidth-intensive operations. Such allocation of duties is exemplary only. In some implementations, the high-speed controller 340 is coupled to the memory 320, the display 380 (e.g., through a graphics processor or accelerator), and to the high-speed expansion ports 350, which may accept various expansion cards (not shown). In some implementations, the low-speed controller 360 is coupled to the storage device 330 and low-speed expansion port 370. The low-speed expansion port 370, which may include various communication ports (e.g., USB, BLUETOOTH®, Ethernet, wireless Ethernet), may be coupled to one or more input/output devices, such as a keyboard, a pointing device, a scanner, or a networking device, such as a switch or router, e.g., through a network adapter.

The computing device 300 may be implemented in a number of different forms, as shown in the figure. For example, it may be implemented as a standard server 300a or multiple times in a group of such servers 300a, as a laptop computer 300b, or as part of a rack server system 300c.

Various implementations of the systems and techniques described here can be realized in digital electronic circuitry, integrated circuitry, specially designed ASICs (application specific integrated circuits), FPGAs (field-programmable gate arrays), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit), or an ASIC specially designed to withstand the high radiation environment of space (known as "radiation hardened", or "rad-hard").

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims.

What is claimed is:

1. A method for determining respiratory induced blood mass change from a four-dimensional computed tomography, the method comprising:
    receiving, at a data processing hardware, four-dimensional computed tomography image set including a first three-dimensional computed tomography image of a volume and a second three-dimensional computed tomography image of the volume;
    determining, at the data processing hardware, a spatial transformation from the first three-dimensional computed tomography image to the second three-dimensional computed tomography image by determining a deformable image registration image in the form of a displacement vector field, the displacement vector field indicative of lung motion induced by breathing of a patient, wherein the displacement vector field includes a plurality of vectors, each of the vectors indicative of a transformation of a point between the first three-dimensional computed tomography image and the second three-dimensional computed tomography image;
    determining, at the data processing hardware, a blood mass change within the volume based on the spatial transformation; and
    outputting, from the data processing hardware, a respiratory-induced blood mass change image based on the determined blood mass change.

2. The method of claim 1, further comprising executing, at the data processing hardware, a deformable image registration (DIR) function on the first three-dimensional computed tomography image and the second three-dimensional computed tomography image.

3. The method of claim 2, further comprising segmenting, at the data processing hardware, the first three-dimensional computed tomography image and the second three-dimensional computed tomography image.

4. The method of claim 1, further comprising:
    delineating, by the data processing hardware, a first plurality of subvolumes within the first three-dimensional computed tomography image; and
    warping, by the data processing hardware, each of first plurality of the subvolumes onto the second three-dimensional computed tomography image.

5. The method of claim 4, wherein the step of warping each of the first plurality of subvolumes includes estimating a mass change for each of the subvolumes.

6. The method of claim 1, wherein the first three-dimensional computed tomography image is taken at a first phase of a respiratory cycle and the second three-dimensional computed tomography image is taken at a second phase of the respiratory cycle.

7. The method of claim 6, wherein the first phase is a full inhale phase and the second phase is a full exhale phase.

8. The method of claim 1, wherein determining the blood mass change within the volume includes determining, by the data processing hardware, a sum of a blood mass change for a plurality of subvolumes of the volume.

9. A system comprising:
data processing hardware; and
memory hardware in communication with the data processing hardware, the memory hardware storing instructions that when executed on the data processing hardware cause the data processing hardware to perform operations comprising:
receiving four-dimensional computed tomography image set including a first three-dimensional computed tomography image of a volume and a second three-dimensional computed tomography image of the volume;
determining a spatial transformation from the first three-dimensional computed tomography image to the second three-dimensional computed tomography image by determining a deformable image registration image in the form of a displacement vector field, the displacement vector field indicative of lung motion induced by breathing of a patient, wherein the displacement vector field includes a plurality of vectors, each of the vectors indicative of a transformation of a point between the first three-dimensional computed tomography image and the second three-dimensional computed tomography image;
determining a spatial distribution of blood mass change within the volume based on the spatial transformation; and
outputting a respiratory-induced blood mass change image based on the determined spatial distribution of blood mass change.

10. The system of claim 9, wherein the operations further comprise executing a deformable image registration (DIR) function on the first three-dimensional computed tomography image and the second three-dimensional computed tomography image.

11. The system of claim 10, wherein the operations further comprise segmenting the first three-dimensional computed tomography image and the second three-dimensional computed tomography image.

12. The system of claim 9, wherein the operations further comprise:
delineating a first plurality of subvolumes onto the first three-dimensional computed tomography image; and
warping each of first plurality of the subvolumes onto the second three-dimensional computed tomography image.

13. The system of claim 12, wherein the operation of warping each of the first plurality of subvolumes includes estimating a mass change for each of the subvolumes.

14. The system of claim 9, wherein the first three-dimensional computed tomography image is taken at a first phase of a respiratory cycle and the second three-dimensional computed tomography image is taken at a second phase of the respiratory cycle.

15. The system of claim 14, wherein the first phase is a full inhale phase and the second phase is a full exhale phase.

16. The system of claim 9, wherein the operation of determining the blood mass change within the volume includes determining, by the data processing hardware, a sum of a blood mass change for a plurality of subvolumes of the volume.

* * * * *